United States Patent [19]

Lee

[11] Patent Number: 5,367,054

[45] Date of Patent: Nov. 22, 1994

[54] LARGE-SCALE PURIFICATION OF EGG IMMUNOGLOBULIN

[75] Inventor: Young-Zoon Lee, Cincinnati, Ohio

[73] Assignee: Stolle Research & Development Corp., Cincinnati, Ohio

[21] Appl. No.: 45,061

[22] Filed: Apr. 12, 1993

[51] Int. Cl.$^5$ .......................... C07K 3/20; C07K 3/22; A61K 37/04; A61K 39/385

[52] U.S. Cl. ..................... 530/359; 530/350; 530/382; 530/387.1; 530/413; 530/425

[58] Field of Search ............... 530/387, 382, 359, 350, 530/387.1, 413, 425

[56] References Cited

U.S. PATENT DOCUMENTS

Re. 31,268 6/1983 Hanson .............................. 424/174

FOREIGN PATENT DOCUMENTS 0346217 12/1989 European Pat. Off. .
9013817 11/1990 WIPO .

OTHER PUBLICATIONS

Nakai et al. (1991) Journal of Food Science 56, pp. 1537–1541.
Nakai et al. (1992) Journal of Food Science 52, pp. 629–634.
Perosa et al. (1990) Journal of Immunological Methods, 128, pp. 9–8.

Primary Examiner—Herbert J. Lilling
Attorney, Agent, or Firm—Sterne, Kessler, Goldstein & Fox

[57] ABSTRACT

The present invention relates to methods for the isolation and purification of immunoglobulins or fragments thereof or other biologically active factors from non-immune or immune egg yolk, by extracting the yolk with a composition containing one or more medium-chain fatty acids. The present methods provide egg immunoglobulin of high purity and high yield.

15 Claims, 2 Drawing Sheets

LARGE-SCALE PURIFICATION OF EGG IMMUNOGLOBULIN

FIELD OF THE INVENTION

The invention relates to methods of purifying proteins from egg components obtained from eggs produced by immunized or non-immunized avian animals, reptiles, amphibians or fish including, for example, chickens.

BACKGROUND OF THE INVENTION

Although antibiotics have been used successfully to prevent infection, constant use of these agents has been discouraged because some have side effects (DuPont et al., *Rev. Infect. Dis.* 4:533 (1982); Sack, R. B., *Rev. Infect. Dis.* 8:S160 (1986)). It has also been found that some microbes develop resistance to antibiotics, rendering them ineffective (McDougald, L. R., Control of Coccidiosis in Chickens: Chemotherapy. in *Coccidiosis of Man and Domestic Animals*, P. L. Long, ed., CRC Press, Florida, 1990, p.307). Passive immunization is an alternative method of protection from infection. Antibodies are safe, natural products that bacteria will not build up resistances against and therefore can be fed continually. No side effects were observed by Tacket et al., *New Eng. J. Med.* 3;18:1240 (1988) when using milk immunoglobulin concentrate as an effective prophylactic against traveler's diarrhea. Fortification of food products with specific immunoglobulins or oral vaccines containing immunoglobulins would be an innovative way to help alleviate the problems associated with antibiotics.

Egg yolk is recognized as a very good source of specific antibodies. The advantages it offers over conventional antibody production are well documented. These include the potential of producing more specific antibodies against antigens in birds and mammals (Jensenius et al., *J. Immunol. Methods* 46:63 ( 1981 )), low cost, convenience ( Polson et al., *Immunol. Commun.* 9:475 (1980)) and, what is becoming more important, compatibility with modern animal protection regulations (Gottstein, B. et al., *Z. Parasitenkunde* 71:273 (1985)). It has also been reported that production and maintenance of higher levels of specific antibodies is relatively easy (Orlans, E. *Immunology* 12:27 (1967); Rose et al., *Eur. J. Immunol.* 4:521 (1974)).

Hen serum IgG is transferred to its egg yolk and provides its offspring with acquired immunity. Thus, it is possible to obtain pathogen-specific egg yolk antibodies from eggs laid by hens immunized against the specific antigens. Egg yolk immunoglobulin (IgY) content of chicken eggs is about 100–150 mg/egg (Rose et al., *Develop. Comp. Immunol.* 5:115–20 (1981)), an amount which is remarkably higher than the antibody (IgG) content in the same volume of mammalian serum or milk. IgY differs from mammalian IgG in molecular size (168,000), isoelectric point (more acidic) (Schmizu et al., *Biosci, Biotech. Biochem.* 56:270–274 (1992)) and in binding ability with mammalian complement and protein A (none) (Martin et al., *Can. J. Biochem. Physiol.* 35:241 (1957)). IgY is also known as γ-livetin and exists in egg yolk together with two other important water-soluble proteins, α-livetin (chicken serum albumin) and β-livetin (α-2-glycoprotein) and various I ipoproteins (LDL and HDL) which are the major components of egg yolk (Martin et al., *Can. J. Biochem. Physiol* 35:241 (1957)). Therefore, the first step in the isolation of IgY is to separate the water-soluble proteins from lipoproteins. Water-soluble proteins constitute 42.4% of the total proteins in egg yolk (Osuga et al., "Egg Proteins: In Food Proteins, J. R. Whitaker and S. R. Tannenbaum eds., AVI Pub. Co., Westport, Conn. (1977)).

Many methods have been used for the isolation and purification of immunoglobulins from egg yolk (Martin et al., *Can. J. Biochem. Physiol.* 35:241 (1957); Martin et al., *Can. J. Biochem Physiol.* 36:153 (1958); Jensenius et al., *J. Immunol. Methods* 46:63 (1981); Bade et al., *J. Immunol. Methods* 72:421 (1984); Polson et al., *Immunol. Invest.* 14:323 (1985); Hassl et al., *J. Immunol. Methods* 110:225 (1988)). Hatta et al. (*Agric. Biol. Chem.* 54:2531 (1990)) used food-grade natural gums (e.g., carrageenan) to remove yolk lipoprotein as a precipitate and to recover IgY in the water-soluble fraction from egg yolk. Kwan et al., *J. Food Sci.* 56:1537 (1991) used water dilution to fractionate water-soluble from water-insoluble components of egg yolk. About 15–21% of the total proteins were recovered in the supernatant of ten-fold diluted yolk, with approximately 60% recovery of IgY activity. Recently, Akita et al., (*J. Food Sci.* 57:629(1992)) reported that egg yolk diluted six-fold with water at pH 5.0–5.2 and incubated at 4° C. for 6 hr yielded 100 mg of electrophoretically-pure IgY per egg by a combination of ultrafiltration, gel filtration and ion exchange chromatography.

Passive protection of neonatal piglets against fatal enteric coli bacillosis was achieved with powder preparations of specific antibodies against K88, K99, and 987P fimbrial adhesions of enterotoxigenic *Escherichia coli* (Yokoyama et al., *Infect. Immunol.* 60:998 (1992)). The antibody powders were obtained by spray-drying the water-soluble protein fraction of egg yolks from immunized hens after the lipid components were precipitated with an aqueous dispersion of acrylic resins (Eudragit L30D-55; Rhom Pharma).

Using the small animal model, passive protection of suckling mice against human rotavirus infection was achieved with the use of immunoglobulin from the yolks of eggs of rotavirus-immunized hens (Ebina et al., *Microbiol. Immunol.* 34:617 (1990)). Egg yolks separated from albumen were mixed with the same volume of distilled water. After homogenization, yolks were filtered through gauze. The precipitate fraction was found to be composed of lipoprotein, and the supernatant fraction was composed of water-soluble protein. Water-soluble protein fractions (0.123 mg IgY/mg protein) were applied to a DEAE-Sephacel ion-exchange chromatography column and eluted with 200 mM phosphate buffer, pH 8.0. Fractions of a 280 nm peak (0.562 mg IgY/mg protein) were precipitated by saturated ammonium sulphate 3 times and dialyzed with 20 mM phosphate buffer, pH 8.0. Purified IgY fractions were finally filtered through a 0.45 μm membrane filter and freeze-dried.

Most of the methods mentioned, while perhaps satisfactory on a laboratory scale, are unsuited to scaling to a high volume procedure for the production of kilogram levels of food-grade antibodies. Chanutin and coworkers (*Arch. Biochem. Biophys.* 89:220 (1960)) observed the precipitation of plasma proteins by short-chain fatty acids at pH 4.2. Steinbuch and Audran (*Arch. Biochem. Biophys.* 134:279 (1969)) indicated that precipitation of the bulk of plasma proteins with caprylic (octanoic) acid can be done without adversely affecting IgG, ceruloplasmin, and part of the IgA.

Medium-chain triglycerides (MCT) are the basis of a new group of fats known as structured lipids which have advantages in clinical nutrition and the treatment of disease (Kennedy, J. P., *Food Technol.* 45:76 (1991)). MCT oil is a saturated fat composed of C8 (caprylic) and C10 (capric) fatty acids. It is manufactured from the fractionated medium-chain fatty acids of vegetable oils such as coconut and palm kernel oil. Medium-chain fatty acids are not incorporated into chylomicrons, therefore they are not likely to be stored in the adipose tissue of the body. Instead, they are oxidized for energy in the liver as are carbohydrates and provide a dense source of calories which the body can readily use. This makes MCT ideal for anyone with high energy requirements. In the flavor industry, MCT's are frequently used as a solvent, carrier or diluent to cut concentrated essential oils and flavors when high stability, low viscosity and blandness are desired. MCT's are also used as carriers for colors, vitamins, and pharmaceuticals. Caprylic acid is a natural component of chicken eggs, found at 0.6% in the whole egg and 0.15 % in egg yolk (Cotterill et al., *Poult. Sci.* 56:1927 (1977)).

SUMMARY OF THE INVENTION

Figure 1:
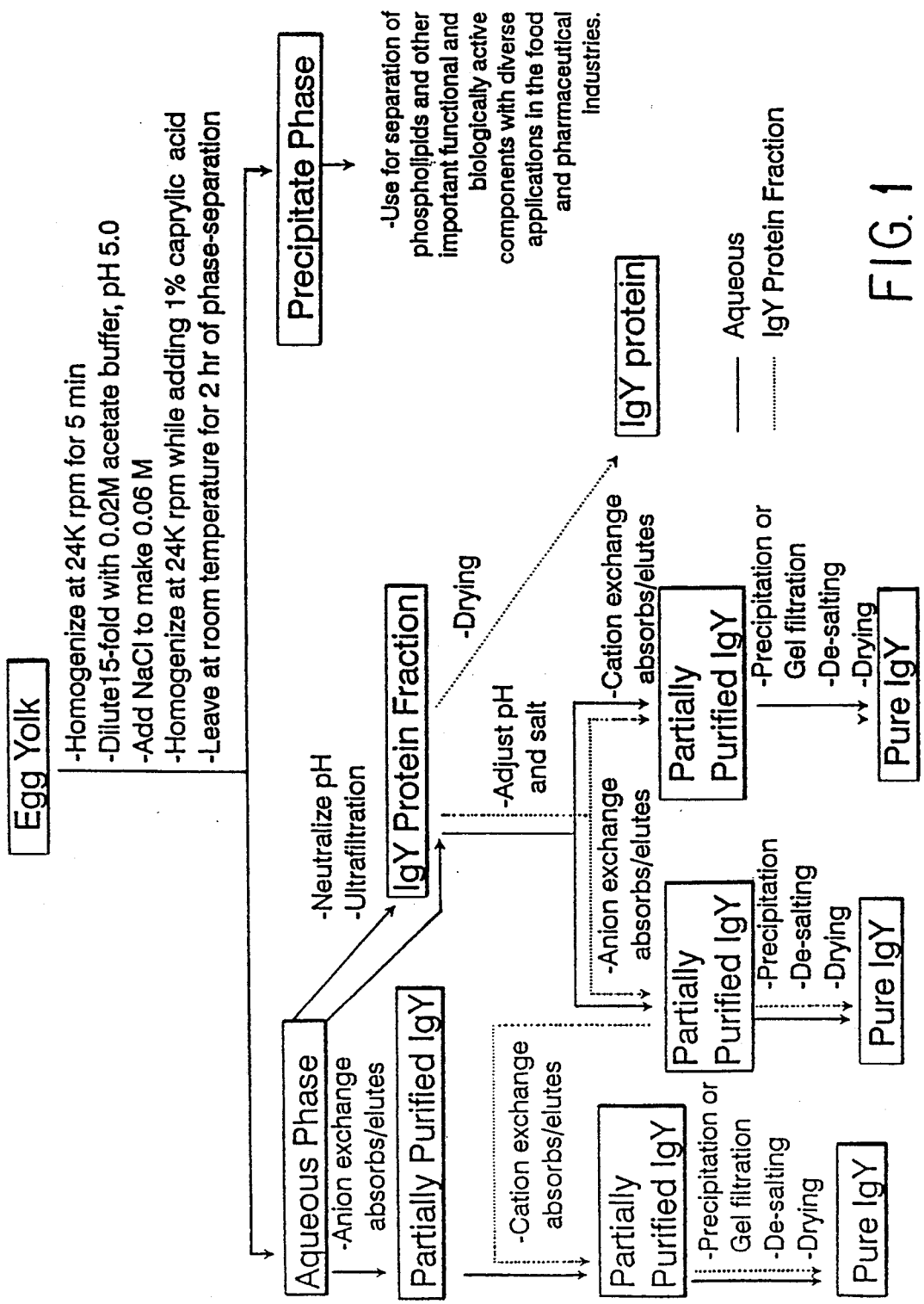
FIG. 1 is a schematic diagram of the methods of the present invention.

The present invention is directed to improved methods for the isolation and purification of egg yolk immunoglobulin or derivatives thereof from eggs produced by immunized or non-immunized arian animals, reptiles, amphibians or fish. The present method is particularly useful for purifying egg yolk immunoglobulins (mainly IgY, IgA and IgM) from a large volume of immune or non-immune egg yolk. The purified products can be used for pharmaceutical purposes, e.g. passive immunization, or as a health food ingredient.

The present invention is also directed toward a method for recovering biologically active components including, for example, ovotransferrin, δ-livetin, vitamin-binding proteins, apovitellenins I-VI, α-lipovitellin, β-lipovitellin, phosvitin, pigments, natural antioxidants, lecithin, enzymes, choline esterase, acid phosphatase, lysozyme, acid protease, anti-inflammatory factor, growth factor, interleukin 1 (IL- 1), IL-2, IL-3, interferons, glucosamine, hexoses, oligosaccharides, phospholipids and sialic acids from egg yolk including the steps of extraction.

The present invention is a method for the purification of egg immunoglobulin including the steps of extraction with e.g. medium-chain fatty acids, and further purification with e.g. ultrafiltration and/or ion exchange chromatography and/or protein precipitation and/or gel filtration and/or desalting and/or drying.

The present invention is directed toward a method for purification of immunoglobulin egg yolk, including the steps of extracting the egg yolk immunoglobulin using medium-chain fatty acids including, for example, caprylic acid, to obtain an immunoglobulin-containing aqueous phase, followed by the steps of subjecting the aqueous phase to ion-exchange chromatography, for example, anion exchange chromatography; subjecting the recovered immunoglobulin fraction to additional ion-exchange chromatography, for example, cation exchange chromatography; subjecting the recovered immunoglobulin to protein precipitation, e.g., ammonium sulfate precipitation; and subjecting the recovered immunoglobulin to gel filtration and/or de-salting by dialysis or diafiltration.

The present invention is further directed toward a method of purification including the steps of extraction with medium-chain fatty acids and ultrafiltration of the resultant aqueous phase before processing as above.

The invention provides processes for obtaining substantial amounts of immunoglobulins in usable form from large volumes of egg yolk, in simple steps, to provide a product of high purity and high yield. The two major products are IgY protein obtained as a retentate from ultrafiltration of the aqueous phase and the pure IgY obtained as summarized above. Major segregation of the immunoglobulin product from egg yolk materials, including lipid, lipoprotein and other proteins is achieved by extraction with 0.5–2.0% medium-chain fatty acids.

DETAILED DESCRIPTION OF THE PREFERRED EMBODIMENTS

Definitions

The terms "pure" and "purified" intended to be equivalent. A "pure" or "purified" immunoglobulin (or fragment thereof or other biologically active factor) means an immunoglobulin (or fragment thereof or other biologically active factor) that is substantially free of other biological macromolecules or structural components normally associated with the immunoglobulin or fragment thereof in its natural state in the whole egg. Such "other components" include e.g. other proteins, carbohydrates, or lipids.

By the terminology "immunoglobulin or fragment thereof" is intended antibody that is transferred across the follicular epithelium of the avian, reptile, amphibian or fish ovary and accumulated in the yolk during oogenesis. There are three classes of egg yolk immunoglobulin, IgY, IgA, and IgM. Biologically active fragments of these immunoglobulins are well recognized in the art and include, for example, the Fab fragment (having the antigen binding site), the Fc fragment (the protein domain involved in immune regulation (the fragment that crystallizes)), and the Fc' fragment. The term "biologically active factors" is intended to include anti-inflammatory factor, growth factor, interleukin I(IL-1), IL-2, IL-3, and interferons.

By the terminology "medium-chain fatty acids" is intended any fatty acid or complexes thereof having from 6 to 12 carbon atoms (more preferably 8 or 10 carbon atoms), including, for example, capric acid, caprylic acid, or medium-chain triglyceride oil, and solutions containing medium-chain triglyceride oil. Medium-chain triglyceride oil is manufactured from fractioned medium-chain fatty acids of vegetable oils including for example, coconut and palm kernel oil.

By the terminology "immune eggs" is intended eggs from any egg-producing members of the avian, reptile, amphibian or fish family which have been immunized, such members preferably being, but not limited to, domesticated chickens (genus *Gallus*).

Methods for the management, husbandry, handling and vaccination of avians, reptiles, amphibians and fish are known in the art (see, for example, The Merck Vetrinary Manual, sixth edition, C. M. Fraser, ed., Merck & Co., Rahway, N.J., 1986; Antibodies, A Laboratory Manual, E. Harlow et al., eds., Cold Spring Harbor Laboratory, 1988). The response of the fish immune system may be influenced by the water temperature.

Avian animals include poultry and fowl (such as chickens, turkeys, geese, ducks and caged birds).

Reptiles are represented by members of the class Reptilia which is divided into four orders. Crocodilia includes the alligators, caimans, crocodiles, and gavials; Chelonia includes tortoises and turtles; Squamata includes lizards and snakes; and the Rhynchocephalia contains the tuatara as the sole species in the order. In Reptiles, internal fertilization occurs, and development of the embryo takes place within an amnionic egg either externally (oviparity) or internally (ovoviviparity/viviparity).

Amphibians are cold-blooded vertebrates with characteristics between fish and reptiles, having gilled aquatic larvae and air-breathing adults. Amphibian animals include frogs, toads, and salamanders.

The methods of the present invention are intended to provide egg immunoglobulins of about 90% purity, preferably of >90% purity (wherein any remaining components are benign) and a high yield range of 60 % to 90 %, preferably from 70% to 90% in practical kilogram quantities from large volumes of immune egg yolk. All of the methods employ one or more of the following processes: dilution with water and/or buffer, phase separation, pH adjustment, ultrafiltration, anion exchange chromatography, cation exchange chromatography, protein precipitation, gel filtration chromatography, desalting and drying.

Suitable medium-chain fatty acids for phase separation include caproic acid, caprylic acid, caprio acid, and lauric acid alone or in complexes such as medium-chain triglycerides (MCT) and MCT oils or solutions thereof containing one or more of the foregoing oils: palm-kernel, cohune, coconut, or babassu. Most preferably, caprylic acid is used.

Extraction and phase separation are the initial steps in producing a water-soluble-protein (IgY) aqueous phase. Immune egg yolk is diluted 5–30 times with water and/or buffer, preferably starting with a 7.5-fold dilution with deionized water (DIW) before further dilution. The diluted egg yolk is then homogenized for at least 3 minutes, preferably for 5 minutes, at about 3,500–30,000 rpm, preferably 24,000 rpm at between 4° C. and 50° C. This homogenate is further diluted up to 4-fold with 0.01–1.0 M acid buffer including for example, acetate, citrate or phosphate buffer, to give a final pH of about 4–6, and a final salt concentration of about 0.01–0.4 M, most preferably a 2-fold dilution with 0.04 M acetate buffer, pH 5.0, and final salt concentration of 0.06 M NaCl. The diluted homogenate is again homogenized as above for 3–20 minutes, preferably 3–4 minutes while adding medium-chain fatty acids, including, for example, caprylic acid, to a final concentration of about 0.5–2.0 %, preferably 1%. After phase separation, the immunoglobulins are present in the bottom aqueous layer (aqueous phase), and the majority of other components including most lipoproteins, lipids, and yolk enzymes (for example choline esterase), are in the lipidic top flocculate layer (precipitate phase). Immunoglobulins contained in the aqueous phase are then further purified by ultrafiltration and/or ion exchange chromatography.

For ultrafiltration, the aqueous phase from phase separation is pH adjusted to near neutral and then ultrafiltered or diafiltered and concentrated, preferably through a 30K–300K molecular weight cut off (MWCO) ultrafiltration membrane, more preferably a 30K molecular weight cut off ultrafiltration membrane. The resulting retentate containing IgY can be either dried and used as IgY protein powder or it can be further purified by ion exchange chromatography. Suitable ultrafiltration membranes to use can easily be chosen by one of ordinary skill in the art and include, for example: S10Y30 and S10Y100 spiral wound membranes and H10P30-20 and H5P100-43 hollow fiber membranes (Amicon, Inc.), titanium dioxide Formed-in-Place membranes (DuPont, Co.), Sartocon II (Sartorius), Pilot 1000 ultrafiltration system (BioKen), regenerated cellulose membrane (Millipore), Filtron cassette system (Filtron), or Hallo fiber membrane (Romicon).

For ion-exchange column chromatography as described in this patent, ligands of general affinity can be used to achieve the desired selectivities and binding properties. Fast-flow base matrixes, for example, cellulose with ligands for high capacity absorption of the desired protein (e.g. DE and CM Cellulose Fast Flow, weak anion- and weak cation- exchangers), are ideal for large-scale IgY separation as described in this patent.

The ultrafiltration retentate (IgY protein fraction) is initially applied to an anion-exchange resin under conditions wherein the immunoglobulins do not adsorb to the resin. The IgY-containing unbound fraction thus obtained is either precipitated (or gel filtrated), de-salted and dried for product, or else applied to a cation-exchange column wherein the desired product (i.e., IgY) is adsorbed and then eluted from the cation-exchange resin to obtain a cation column fraction containing the desired product. The manipulation and optimization of such conditions is within the knowledge of one of ordinary skill in the art.

Alternatively, the aqueous phase obtained from phase separation can be first partially purified using ion-exchange chromatography. The aqueous phase is applied to an anion-exchange column under conditions wherein undesired products are adsorbed to the resin and the desired product is not adsorbed. The desired unbound IgY protein fraction is collected for further processing (with or without first cation-exchange chromatography) by protein precipitation or gel filtration, de-salting and drying. The manipulation and optimization of such conditions is within the knowledge of one of ordinary skill in the art. Suitable anion exchange chromatography materials include, for example: DE92 (diethylaminoethyl cellulose, Whatman), DEAE-Cellulose (Sigma), Bakerbond ABX 40μ (J. T. Baker, Inc.), Fractogel EMD DEAE-650 (EM Separations), TSK gel DEAE-SPW (Fosohaas), DEAE-Sepharose CL-6B (Pharmacia), Chelating Sepharose (Pharmacia), DEAE Mere Sep. 1000 (Millipore), Q-HyperD and DEAE Spherodex (Sepracor). Other suitable anion-exchange chromatography materials, as well as the selection and use of these materials for the present application, are known to those of ordinary skill in the art.

After anion-exchange chromatography, the purified fractions can be desalted and either dried or further purified, or can be further purified by cation-exchange chromatography as discussed above. Suitable cation-exchange resins include, for example: CM52 Cellulose (Whatman, Inc.), CM-Sepharose (Pharmacia), S-HyperD and CM Spherodex (Sepracor). Other suitable materials for use in cation-exchange chromatography are within the knowledge of one of ordinary skill in the art, and can be readily selected and used by one of ordinary skill in the art for purposes of the present invention.

Purified fractions obtained from cation-exchange chromatography may be further processed by subjecting to protein precipitation including, for example, precipitation using ammonium sulfate, polyethylene glycol ethanol, sodium sulfate, or acetone, and/or gel filtration chromatography to yield a final purified product after de-salting and drying. Methods for precipitating proteins from solution using ammonium sulfate precipitation are known to one of ordinary skill in the art. For example, suitable methods for ammonium sulfate precipitation include methods disclosed in Harlow, E. and D. Lane. *Antibodies: A Laboratory Manual* pp. 298–299 (1988) incorporated herein by reference.

After protein precipitation, antibody solution obtained may be further purified by gel filtration. Suitable gel filtration methods, the selection of gel filtration materials, and the application of such to the present invention, are within the knowledge of one of ordinary skill in the art. Suitable methods and materials are set forth in Harlow. E. and D. Lane *Antibodies: A Laboratory Manual* p. 308 (1988), incorporated herein by reference.

The partially pure IgY or pure immunoglobulin fractions that were obtained by up to 1.0 M NaCl elution or that have been protein precipitated should be de-salted and, preferably, dried before use as product. De-salting can be done by a number of means, e.g., dialysis or diafiltration. Dialyzing fractions twice in, for example, excess 10 mM Na-phosphate buffer, pH 7.0 with stirring at 3°–8° C., is sufficient to de-salt fractions when fractions are less than 10% of the dialysis buffer volume. Diafiltration of larger fraction volumes with 2–5 times the fraction volume of, for example, DIW is sufficient for de-salting the purified or partially purified IgY fractions for product.

The yield, concentration, and purity of the obtained pure IgY product can be determined by any of the standard methods known to those of ordinary skill in the art. For example, suitable methods include those described in Harlow et al, *Antibodies: A Laboratory Manual* pp. 553–612+636–681 (1988), incorporated herein by reference.

Although even unimmunized eggs from arian animals, reptiles, amphibians or fish contain immunoglobulin that is capable of being isolated according to the invention, higher levels of such immunoglobulin are extractable from eggs taken from a hyperimmune avian animal, reptile, amphibian or fish. Such hyperimmune eggs are produced by bringing the subjects to a specific state of hyperimmunization by means of a primary immunization followed by periodic booster administrations of specific antigens such as pathogenic or nonpathogenic bacterial, fungal, yeast, parasitic or viral antigens or a mixture of such antigens. Antigens can be natural products such as hormones, proteins, polysaccharides, amino acids, etc., or artificial products, various smaller molecules collectively known as haptens which are bound to larger protein carriers. The eggs produced by animals in the hyperimmunized state are immune eggs.

This hyperimmune state is maintained by administering periodic boosters with sufficiently high doses of specific antigens or mixtures of such antigens. The preferred dosage range should be equal to or greater than 50% of the dosage necessary to cause primary immunization of the animal. Having knowledge of this requirement for developing and maintaining the hyperimmune state, it is within the knowledge of one of ordinary skill in the art to vary the amount of antigen administered, as well as the specific antigen(s) administered, depending upon the animal employed and the desired specificity of the immunoglobulin obtained.

In summary, the process for producing the present immune eggs comprises the following steps:
1. Selection of antigen or antigens.
2. Sensitization of animals by primary immunization.
3. Administering boosters of antigens of appropriate dosage to induce and maintain the hyperimmune state.
4. Collecting eggs from the animal during the hyperimmune state.

Suitable antigens include, for example, bacterial species or subtypes including but not limited to the following: *Staphylococcus. aureus; Staph. epidermidis; Streptococcus. pyogenes,* A. type 1, type 3, type 5, type 8, type 12, type 14, type 18, and type 22; *Aerobacter aerogenes; Escherichia coli; Salmonella enteritidis; Pseudornonas aeruginosa; Haemophilus influenzae; Strep mills; Proteus vulgaris; Shigella dysenteriae; Diplococcus pneumoniae; Propionbacter aches; Strep sanguis; Strep. salivarius;* and *Strep mutans.* The selection of other suitable antigens is within the knowledge of one of ordinary skill in the art. For example, when the IgY isolated from such eggs is used to confer passive resistance, suitable antigens can be selected based on the pathogen(s) one wishes to confer immunization against.

Antigens can be administered by any method which causes sensitization. The preferred method of immunization is by intramuscular injection. The preferred method of administration of the antigens to avian animals (i.e., chickens) is in the breast muscle. The dosage is preferably 1–5 mg of a mixed bacterial vaccine. Repeated immunizations are given at intervals of preferably two weeks, over a suitable period of time, at least two months, to hyperimmunize the animal.

One of ordinary skill in the an can readily determine whether or not the avian animal, reptile, amphibian or fish has become sensitive to the antigen. There are a number of methods known to those of ordinary skill in the art of immunology to test for sensitivity. Please see *Methods of Immunology and Immunochemistry,* Williams, C. A., et al, Academic Press, New York, London (Vols. 1–5) (1977). The appearance of egg antibodies after immunization with the desired antigen is indicative of sensitization. The minimum dose of antigen necessary to induce hyperimmunization depends on the type of antigen used.

The hyperimmune state can be induced and maintained by repeated booster administration of an appropriate dosage at fixed-time intervals, preferably two-week intervals over a two-month period when polyvalent bacterial agents are employed. However, the booster administration must be optimum, otherwise it may induce a state of immune tolerance or less specificity. This will cause the animal to pass from its hyperimmune state to a state of tolerance to the antigen, where the animal will cease to produce specific antibodies.

A combination of different immunization procedures, i.e., intramuscular injection for primary immunization and intravenous injection for booster injections, etc., may be used. Many different combinations of immunization might be employed by those skilled in the art to (1) initially sensitize and (2) induce the hyperimmune state.

The immune eggs produced are collected and egg yolks are separated from the egg whites. Egg yolks are then purified by the methods of the present invention to obtain substantially pure IgY and/or fragments thereof.

Examples of suitable antigens for immunizing hens, according to the present invention are transmissible gastroenteritis-causing bacteria, *Clostridium difficile, Rotavirus, E. coli, Coccidiosis, Salmonella Coleraesuis, S. typhimurium, S. enteritidis, Streptococcus suis, Staphylococcus aureus, Staphylococcus epidermidis, Streptococcus pyogenes* A. Type 8, *Pseudomonas aeruginosa, Proprionibacter aches, Micrococcus luteus, Corynebacterium minutissimum, Candida albicans.*

EXAMPLES

The following examples are intended to illustrate, but not to limit the invention. The sequence of purification steps in the following examples are summarized in FIG. 1. Purification data is presented in Tables 1 and 2, below.

Example 1

Phase Separation of Egg Yolks using Caprylic Acid (CAPS)

Figure 2:
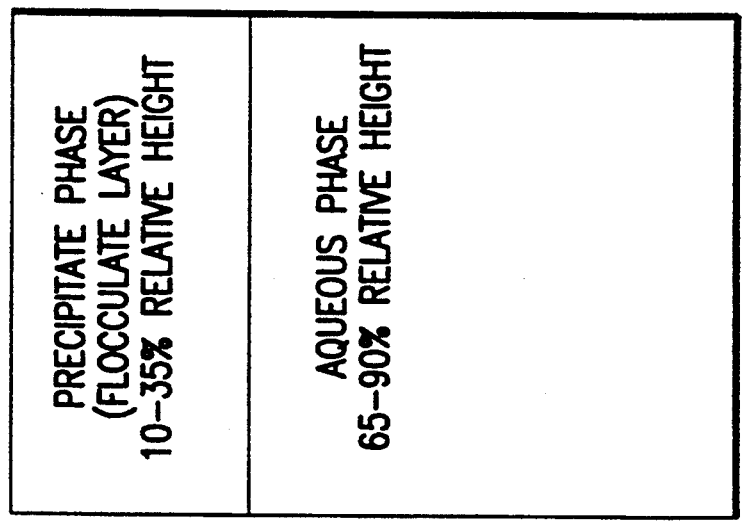
FIG. 2 is a diagrammatical representation of phase separation of egg components by caprylic acid.

Non-immune or immune eggs from Nick's White Leghorn hens immunized against *Candida albicans* were each injected with 16 mg of heat-killed *Candida albicans* bi-weekly starting at 28 weeks of age. Anti-*Candida albicans* specific antibody eggs were produced by these hyperimmune hens and were collected, cracked, and egg yolks were separated from egg whites. The recovered egg yolk was diluted 7.5-fold with deionized water (DIW) and homogenized at 24,000 rpm for 5 rain using a Tekmar Tissumizer Mark II. The resulting yolk-DIW homogenate was further diluted 2-fold with 0.06 M NaCl in 0.04 M acetate buffer, pH 5.0 and homogenized at 24,000 rpm for 3 rain while adding caprylic acid to a final concentration of 1%. The preparation was left at room temperature for 2 hours for phase-separation (see FIG. 2). Caprylic acid and salt addition is an integral part of the phase-separation process in that dilution of egg yolk 15-fold with acetate buffer or water alone neither brings about phase-separation nor recovery of the aqueous phase by filtration. The precipitate phase can be used to extract phospholipids, lecithin, sialic acid and other important functional and biologically active components with diverse applications in the food and pharmaceutical industries. After phase-separation, the immunoglobulins are present in the bottom aqueous phase, and the majority of the other components, including most lipoproteins, lipids and other yolk proteins, remain in the flocculate (precipitate phase). The aqueous phase was adjusted to pH 7.0 with 0.5 M NaOH.

Example 2

Anion-Exchange Column Chromatography of Aqueous Phase to Obtain a Partially Purified IgY The aqueous phase obtained above was 2-fold diluted and adjusted to pH 7.6 using 0.12 M TRIS buffer and applied to a DE92 (Diethylaminoethyl cellulose, Whatman Inc.) anion-exchange column. A 350 ml-glass column from Bio-Rad Co., was pre-equilibrated with approximately 5 column volumes of equilibration buffer (0.06 M TRIS, pH 7.6). The bulk of the antibody was obtained in a single light pink unbound fraction; chromatography running conditions were such that the yellow flavoprotein-binding protein was selectively bound and thus isolated from IgY. After sample application the column was washed with approximately 3 column volumes of the equilibration buffer and then the bound fraction was eluted with approximately 3 column volumes of 0.5 M NaCl in 0.06 M TRIS, pH 7.6. The pink color in the unbound IgY fraction was due to ovotransferrin. The purified fractions were either de-salted and freeze-dried or further processed. Recovery rate and purity of this IgY fraction are 48.4 % and 40.0 % respectively.

Example 3

Cation-Exchange Column Chromatography of Aqueous Phase to Obtain a Partially Purified IgY The IgY-containing aqueous phase obtained in Example 1 was diluted with an equal volume of 0.4 M Na-acetate buffer, pH 5.0 and applied to a CM52 cation-exchange column. A column with a bed volume of 50 ml was pre-equilibrated with approximately 5 column volumes of 0.2 M Na-acetate buffer, pH 5.0. After the sample entered the column, the column was washed with 0.01 M Na-acetate buffer, pH 5.4. The bound fraction was then eluted with a linear salt gradient up to 1.0 M NaCl in 0.2 M Na-acetate buffer, pH 5.0. IgY was in the bound fraction and the unbound fraction contained unknown egg yolk protein, most probably flavoprotein-binding protein. The IgY fraction obtained was either protein-precipitated (Example 9), gel-filtrated (Example 10) or de-salted (Example 11).

Example 4

Sequential Anion-Exchange and Cation-Exchange Column Chromatographies of Aqueous Phase to Further Purify the IgY Aqueous phase from Example I (under conditions from Example 2) was applied through DE92 anion-exchange column chromatography to remove the yellow flavoprotein-binding protein from the unbound IgY fraction. The resulting partially purified IgY fraction (DE92 unbound fraction) is diluted with an equal volume of 0.4 M Na-acetate buffer, pH 5.0 and applied to a CM52 cation exchange column. The IgY is selectively bound to the cation-exchanger allowing the IgY to be further isolated from other compounds. The IgY fraction obtained was either protein-precipitated (Example 9), gel-filtrated (Example 10) or de-salted (Example 11).

TABLE 1

| | Data from Aqueous Phase | |
|---|---|---|
| IgY Fraction | IgY Recovery (%) | IgY Purity (%) |
| 1. Aqueous Phase (Example 1) | 84.4 | 4.3 |
| 2. Anion Exchange (Example 2) | 66.0 | 20 |
| 3. Ammonium Sulfate Precipitation (Example 9) | 48.4 (From Anion) | 40 (From Anion) |

Example 5

Ultrafiltration of Aqueous Phase to Obtain an IgY Protein Fraction

The aqueous phase obtained from egg yolks in Example 1 was pH-adjusted to near 7.0 and diafiltered through either a 30K (Amicon Spiral Wound Y30) or 100K (Amicon Spiral Wound Y100 or Amicon Hollow Fiber P100) molecular weight cut off (MWCO) ultrafiltration membrane using an Amicon DC 10L Ultrafiltration System. The Amicon 30K MWCO ultrafiltration cartridge has a membrane surface area of 10 ft$^2$, and was run near 40 psi inlet and 33 psi outlet pressures (7 psi transmembrane pressure) with a recirculation flow rate of 10.4 L/min and a flux flow rate of 2.3 L/min. During ultrafiltration, the aqueous phase was first diafiltered with 3-fold volume of DIW and then concentrated down to less than two liters. The resulting IgY protein fraction (retentate) was either dried and stored, or further purified by ion exchange column chromatography. The permeate was de-salted and dried for further study.

Example 6

Anion-Exchange Column Chromatography of IgY Protein Fraction from Example 5 to Obtain Partially Purified IgY The IgY protein fraction from Example 5 was diluted 2-fold with 0.12 M TRIS buffer, pH 7.6 and applied to a DE92 (Diethylaminoethyl cellulose, Whatman Inc.) anion-exchange column. A 350 ml-column from Bio-Rad Co., was pre-equilibrated with approximately 5 column volumes of the equilibration buffer (0.06 M TRIS, pH 7.6). The bulk of the antibody was obtained in a single light pink unbound fraction; chromatography conditions were such that a yellow flavoprotein-binding protein was selectively bound and thus isolated from the IgY. After sample application, the column was washed with approximately 3 column volumes of the equilibration buffer and then the bound fraction was eluted with approximately 3 column volumes of 0.5 M NaCl in 0.06 M TRIS, pH 7.6. The pink color in the unbound IgY fraction was due to ovotransferrin. The purified fractions were either de-salted and freeze-dried or further processed. Recovery rate and purity of this IgY fraction are 68.8 % and 88 % respectively.

Example 7

Cation-Exchange Column Chromatography of IgY Protein Fraction from Example 5 to Obtain Partially Purified IgY The IgY protein fraction from Example 5 was diluted by an equal volume of 0.4 M Na-acetate buffer, pH 5.0 and applied to a CM52 cation exchange column. A column with a bed volume of 50 ml was pre-equilibrated with approximately 5 column volumes of 0.2 M Na-acetate buffer. After the sample entered the column, the column was washed with 0.01 M Na-acetate buffer, pH 5.4. The bound fraction was then eluted with a linear salt gradient up to 1.0 M NaCl in 0.2 M Na-acetate buffer, pH 5.0. IgY was in the bound fraction and the unbound fraction was unknown egg yolk protein, most probably flavoprotein-binding protein. The IgY fraction obtained was either protein-precipitated (Example 9), gel-filtrated (Example 10) or de-salted (Example 11).

Example 8

Sequential Anion-Exchange and Carton-Exchange Column Chromatographies of IgY Protein Fraction from Example 5 to Obtain a Partially Purified IgY DE92 anion-exchange column chromatography of IgY protein fraction from Example 5 (under conditions from Example 6) is run to remove the yellow flavoprotein-binding protein from the unbound IgY fraction. The resulting partially purified IgY fraction (DE92 unbound fraction) is diluted with an equal volume of 0.4 M Na-acetate buffer, pH 5.0 and applied to a CM52 cation-exchange column. The IgY is selectively bound to the cation-exchanger allowing it to be isolated from other compounds. The IgY fraction obtained was either protein-precipitated (Example 9), gel-filtrated (Example 10) or de-salted (Example 11).

Example 9

Protein Precipitation of Partially or Further Purified IgY Fractions

The antibody fractions from anion-exchange column chromatography (Examples 2 and 6) were ammonium sulfate-precipitated into two fractions: a pink supernatant fraction and an IgY precipitate fraction. Fifty percent saturated ammonium sulfate was gradually mixed with the fractions and then centrifuged at 17,700 $\times$ g for 15 minutes. The supernatant was decanted off and the precipitate was re-suspended in a small amount of DIW. Fractions were then de-salted as described in Example 10.

Example 10

Gel Filtration Column Chromatography of the IgY Fraction from Cation-Exchange Chromatography The bound antibody fraction from Example 3 was diluted with an equal volume of 2.0 M sodium chloride and chromatographed at room temperature on a column (100 cm $\times$ 2.5 cm) of ACA44 gel equilibrated with 1.0 M NaCl, pH 5.5. A sample volume of 30 ml was applied to the 450 ml gel bed volume column. Fractions (15 ml/tube) were measured at 280 nm. Three peaks were observed, the initial peak was IgY, the second peak was ovotransferrin, and the third peak was $\beta$-livetin. The resulting protein solutions were de-salted as described in Example 11.

Example 11

De-salting of Partially or Further Purified IgY Fractions

Fractions that had been eluted with 1.0 M salt solutions or had been ammonium sulfate precipitated required de-salting before they could be used (or dried). De-salting was achieved by either of two methods, dialysis or diafiltration (using the same ultrafiltration system as described in Example 5). When using ultrafiltration, the fraction for de-salting was loaded into the reservoir and at least 4 volumes of DIW were used for diafiltering before concentrating the sample.

Fractions de-salted in Spectra/Por 2 dialysis membrane tubing (MWCO: 12,000–14,000) were dialyzed in at least 10 times the sample's volume against 10 mM Na-phosphate buffer, pH 7.0, at 4°–8° C. with stirring. One buffer change was required. De-salted fractions were dried as described in Example 12.

Example 12

Drying of IgY Protein Fraction or Purified IgY Fraction

Pure IgY powder was prepared from de-salted fractions from Example 11 (or IgY protein powder was prepared from IgY protein in Example 5) either by freeze-drying or spray-drying, depending upon the volumes to be dried. Smaller volumes were transferred into tared Virtis freeze-drying flasks and shell-frozen then attached to the Virtis FreezeMobile 25 manifold. After drying was completed, the flask was re-weighed and the pure IgY powder was sealed in a plastic bag and stored at −17° C. until use.

For larger volumes, spray-drying can be used under the following conditions:
Inlet Temperature: 60°–195° C.
Outlet Temperature: 50°–90° C.
Flow Rate: 40–700 ml/min.

TABLE 2

Data from IgY Protein Fraction (30K Retentate)

| IgY Fraction | IgY Recovery (%) | IgY Purity (%) |
|---|---|---|
| 1. Aqueous Phase (Example 1) | 84.4 | 4.3 |
| 2. Ultrafiltration (30K) (Example 5) | 75.1 | 16.8 |
| 3. Anion Exchange (Example 6) | 72.5 | 21.5 |
| 4. Ammonium Sulfate Precipitation (Example 9) | 68.8 (From Anion) | 88 (From Anion) |

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for the purification of IgY from non-immune or immune egg yolk comprising the following steps:
   (a) diluting egg yolk 5- to 30-fold with water or buffer;
   (b) homogenizing the diluted egg yolk of step (a) until a uniform mixture is obtained:
   (c) extracting the homogenate of step (b) by adding one or more medium-chain fatty acids to a final concentration sufficient to cause the resultant mixture to separate into an aqueous bottom phase and a precipitate top phase; and
   (d) recovering the aqueous phase of step (c) containing said IgY.

2. The method of claim 1, further comprising time steps of:
   (e) subjecting said aqueous phase of step (d) to ion exchange chromatography; and
   (f) recovering the IgY purified by said ion-exchange chromatography.

3. The method of claim 2, further comprising the steps of:
   (g) subjecting said recovered IgY of step (f) to additional ion-exchange chromatography, wherein the ion-exchanger used in said additional ion-exchange chromatography has an ionic charge at pH 7 that is opposite in sign to that possessed by the ion-exchanger of step (e) at pH 7; and
   (h) recovering the IgY purified by said additional ion-exchange chromatography.

4. The method of claim 3, further comprising the steps of:
   (i) Subjecting said recovered IgY of step (h) to protein precipitation; and
   (j) recovering the IgY purified by said protein precipitation.

5. The method of claim 4, further comprising the steps of:
   (i) subjecting said recovered IgY of step (j) to gel filtration; and
   (l) recovering the IgY purified by said gel filtration.

6. The method of claim 1, further comprising the steps of:
   (e') subjecting said aqueous phase of step (d) to ultrafiltration; and
   (f') recovering the IgY purified by said ultrafiltration.

7. The method of claim 6, further comprising the steps of:
   (g') subjecting said recovered IgY of step (f') to ion-exchange chromatography; and
   (h') recovering the IgY purified by said ion-exchange chromatography.

8. The method of claim 7, further comprising the steps of:
   (i') subjecting said recovered IgY of step (h') to protein precipitation; and
   (j') recovering the IgY purified by said protein precipitation.

9. The method of claim 8, further comprising the steps of:
   (k') subjecting said recovered IgY of step (j') to gel filtration; and
   (l') recovering the IgY purified by said gel filtration.

10. The method of any one of claims 1–8 or 9, wherein said medium-chain fatty acid is a caprylic fatty acid.

11. The method of claim 2, wherein said ion-exchange chromatography of step (e) is anion-exchange chromatography.

12. The method of claims 7, wherein said ion-exchange chromatography of step (G) is anion-exchange chromatography.

13. The method of claim 2, wherein said ion-exchange chromatography of step (e) is cation-exchange chromatography.

14. The method of claim 7, wherein said ion-exchange chromatography of step (G) is cation-exchange chromatography.

15. The method of either claim 4 or claim 8, wherein said protein precipitation is accomplished using either ammonium sulfate or sodium sulfate.

* * * * *